United States Patent
Scholz et al.

(10) Patent No.: US 7,179,948 B2
(45) Date of Patent: Feb. 20, 2007

(54) PROCESS FOR PREPARING TERT-BUTANOL

(75) Inventors: Bernhard Scholz, Marl (DE); Franz Nierlich, Marl (DE); Dieter Reusch, Marl (DE); Silvia Santiago Fernandez, Oberhausen (DE); Andreas Beckmann, Recklinghausen (DE); Wilfried Bueschken, Haltern am See (DE); Alfred Kaizik, Marl (DE)

(73) Assignee: Oxeno Olefinchemie GmbH, Marl (DE)

( * ) Notice: Subject to any disclaimer, the term of this patent is extended or adjusted under 35 U.S.C. 154(b) by 556 days.

(21) Appl. No.: 10/739,086

(22) Filed: Dec. 19, 2003

(65) Prior Publication Data

US 2004/0171891 A1 Sep. 2, 2004

(30) Foreign Application Priority Data

Dec. 19, 2002 (DE) ................ 102 59 413
Jul. 8, 2003 (DE) ................ 103 30 710

(51) Int. Cl.
*C07C 29/04* (2006.01)
*C07C 29/06* (2006.01)
*C07C 27/08* (2006.01)

(52) U.S. Cl. ............... 568/895; 568/896; 568/897; 568/898; 568/899; 568/900; 568/901

(58) Field of Classification Search ............ None
See application file for complete search history.

(56) References Cited

U.S. PATENT DOCUMENTS

| 4,087,471 | A | * | 5/1978 | Bowman et al. ............ 568/899 |
| 4,100,220 | A | * | 7/1978 | Bowman et al. ............ 585/515 |
| 4,307,257 | A | | 12/1981 | Sada et al. ................. 568/899 |
| 4,360,406 | A | * | 11/1982 | Ikeda et al. .................. 203/32 |
| 5,518,699 | A | | 5/1996 | Kashnitz et al. |
| 6,111,148 | A | | 8/2000 | Ogawa et al. .............. 568/899 |
| 2005/0014985 | A1 | | 1/2005 | Grund et al. |

* cited by examiner

Primary Examiner—Sikarl A. Witherspoon
(74) Attorney, Agent, or Firm—Oblon, Spivak, McClelland, Maier & Neustadt, P.C.

(57) ABSTRACT

The invention relates to a process for preparing tert-butanol by reaction of a homogeneous mixture comprising water, tert-butanol and an isobutene-containing hydrocarbon mixture over an acidic ion-exchange resin at from 30 to 120° C., wherein the homogeneous mixture contains, at a proportion by mass of isobutene of above 10%, from 30 to 80% of the maximum amount of water made possible by the solubility of water in the mixture of tert-butanol and the isobutene-containing hydrocarbon mixture.

20 Claims, 3 Drawing Sheets

PROCESS FOR PREPARING TERT-BUTANOL

FIELD OF THE INVENTION

The invention relates to a process for preparing tert-butanol by addition of water onto isobutene in the presence of an acidic ion exchanger.

BACKGROUND OF THE INVENTION tert-Butanol (TBA) is an important product produced on a large industrial scale and is used as solvent and as intermediate for the preparation of methyl methacrylate. It is a precursor for the preparation of peroxides such as peroxy ketals, peresters or dialkyl peroxides having at least one tertiary butyl group. These compounds are used as oxidants and as initiators for free-radical reactions, for example olefin polymerization or crosslinking of plastics. tert-Butanol serves as intermediate in the isolation of pure isobutene from isobutene mixtures. Furthermore, it is a reagent for the introduction of tertiary butyl groups. Its alkali metal salts are strong bases which are used in many syntheses.

Tertiary butanol can be obtained by acid-catalyzed addition of water onto isobutene. Industrial isobutene mixtures frequently further comprise other olefins such as 2-butenes. If these starting materials are used, industrial processes employ conditions in which virtually exclusively the isobutene but not the other olefins are hydrated and secondary reactions such as homooligomerization or heterooligomerization of the olefins are virtually completely suppressed. Such processes are usually carried out in the liquid phase and can be divided into two groups: a) processes in which the reaction is carried out in an aqueous catalyst solution and b) heterogeneously catalyzed processes in which solid catalysts which are insoluble in the reaction phase are used.

Homogeneously catalyzed processes employ sulfuric acid, heteropolyacids, p-toluenesulfonic acid or other strong acids as catalyst. These highly active homogeneous catalysts usually form a homogeneous phase with the reaction product, so that the catalyst cannot be separated off mechanically. In some processes, a solvent is additionally used. If the tertiary butanol is isolated from the reaction solution by distillation, the yield is reduced by the backreaction and the formation of by-products.

Heterogeneously catalyzed processes are frequently carried out using acidic ion exchangers as catalysts.

EP 0 579 153 describes a process in which an aqueous solution of a sulfonated polymer (polystyrenesulfonic acids or polyvinylsulfonic acids having molar masses of from 1 000 to 100 000 g/mol) is used as catalyst. Isobutene or the isobutene-containing starting material and the catalyst phase flow concurrently through the reactor. The output from the reactor consists of two phases and separates into a tert-butanol-containing organic upper phase and the catalyst phase. The organic phase is worked up by distillation to isolate tert-butanol. Water is added to the catalyst phase to replace the water which has been consumed and the catalyst phase is then recirculated to the reactor.

The hydration of isobutene to form tert-butanol with the aid of solid acidic catalysts which are soluble neither in the starting materials nor the products has the advantage that the reaction mixture is free of acid and can be worked up to isolate tert-butanol without losses caused by redissociation or other secondary reactions. The reaction proceeds at the surface of the catalyst. For a reaction to occur, both reactants have to be present simultaneously at the active site of the catalyst. This is made relatively difficult by water and isobutene or an isobutene-containing hydrocarbon mixture not being miscible with one another. To obtain acceptable conversions, use is made of solvents which make it possible to obtain a homogeneous mixture of water and isobutene feed mixture.

DE 30 31 702 describes the use of methanol as solvent for this purpose both for water and for isobutene or an isobutene-containing hydrocarbon mixture. tert-Butanol and methyl tert-butyl ether are obtained side by side as products.

In EP 0 010 993, aliphatic carboxylic acids having from 1 to 6 carbon atoms are used as solvents for both starting materials. The tertiary butyl esters of these acids are formed as by-products and have to be hydrolyzed to tert-butanol and carboxylic acids.

DE 030 31 702 uses sulfolanes and U.S. Pat. No. 4,327,231 uses polyhydric alcohols of the neo type, for example neopentyl glycol. These solvents have to be separated off from the tert-butanol. In addition, there is a risk of the solvent used being decomposed in long-term operation of such a plant.

WO 99/33775 describes a process for preparing tert-butanol by reaction of a mixture comprising water, tert-butanol and isobutene or an isobutene-containing hydrocarbon mixture over a cation-exchange resin in a multistage series reactor. The reaction temperature in the individual reactors is below 65° C. Part of the intermediate product from the first reactor is recirculated to the inlet of the same reactor. The recirculation ratio (the amount of intermediate product mixture which is recirculated to the first reactor divided by the amount of feed mixture) is from 1.8 to 10 and the proportion by weight of tert-butyl alcohol in the feed mixture of tert-butyl alcohol and hydrocarbon mixture (sum of isobutene and any other hydrocarbons) at the inlet of the first reactor is from 0.5 to 3.5. The part of the mixture from the first reactor which has not been recirculated flows without intermediate introduction of water through two further reactors in a single pass. The crude product from the last reactor is worked up by distillation. If desired, part of the tert-butanol obtained is recirculated to the first reactor.

A disadvantage of this process is the low space-time yield. The production rate of tert-butanol in the first reactor (operation with product recirculation) is, according to examples 1 to 6, from 0.078 to 0.085 kg per hour per liter of catalyst (at an isobutene concentration at the inlet of from 8.3 to 16.2% by mass and conversions of from 60.2 to 66.1%).

DE 30 25 262 describes a process for preparing TBA using a three-component mixture of water/isobutene/TBA. The process is preferably carried out at or nearby the border of the miscibility gap of this system, but can also be carried out in a heterogeneous and homogeneous region around the miscibility gap. The working range of the process is described by a triangular diagram, and there is wide variability of the composition of the mixture both in the heterogeneous and homogeneous phases because of the ternary mixture.

The compositions of this mixture in the homogeneous, i.e. single-phase region begin at the compositions having the maximum water content (solubility limit of water in the mixture, achievable by means of water separators) and end at mixtures having a low water content (less than about 5% based on the solubility limit).

The ternary mixture of isobutene-containing hydrocarbon/water/tert-butanol having a varying proportion of isobutene in the hydrocarbon mixture therefore leaves open, with the aid of DE 30 25 262, a large number of possible combinations for preparing tert-butanol highly selectively and at satisfactory reaction rates in the presence of a homogeneous catalyst. However, to obtain high reaction rates and selectivities, mixtures whose water contents are close to the solubility limit are preferably used in DE 30 25 262.

SUMMARY OF THE INVENTION

Since the known processes which use acidic cation-exchange resins as catalyst offer a simple work-up but are not satisfactory in terms of the space-time yield and/or selectivity, it is an object of the invention to provide a process which makes it possible to obtain tert-butanol from isobutene or isobutene-containing mixtures with good space-time yields and selectivity at a high isobutene conversion.

It has surprisingly been found that reaction rate, selectivity and space-time yield in the reaction of a homogeneous mixture comprising water, tert-butanol and isobutene or an isobutene-containing hydrocarbon mixture over an acidic ion-exchange resin to form tert-butanol can be increased when the feed mixture contains less than the amount of water which is possible on the basis of the solubility of water in the ternary mixture.

DETAILED DESCRIPTION OF THE INVENTION

Figure 1:
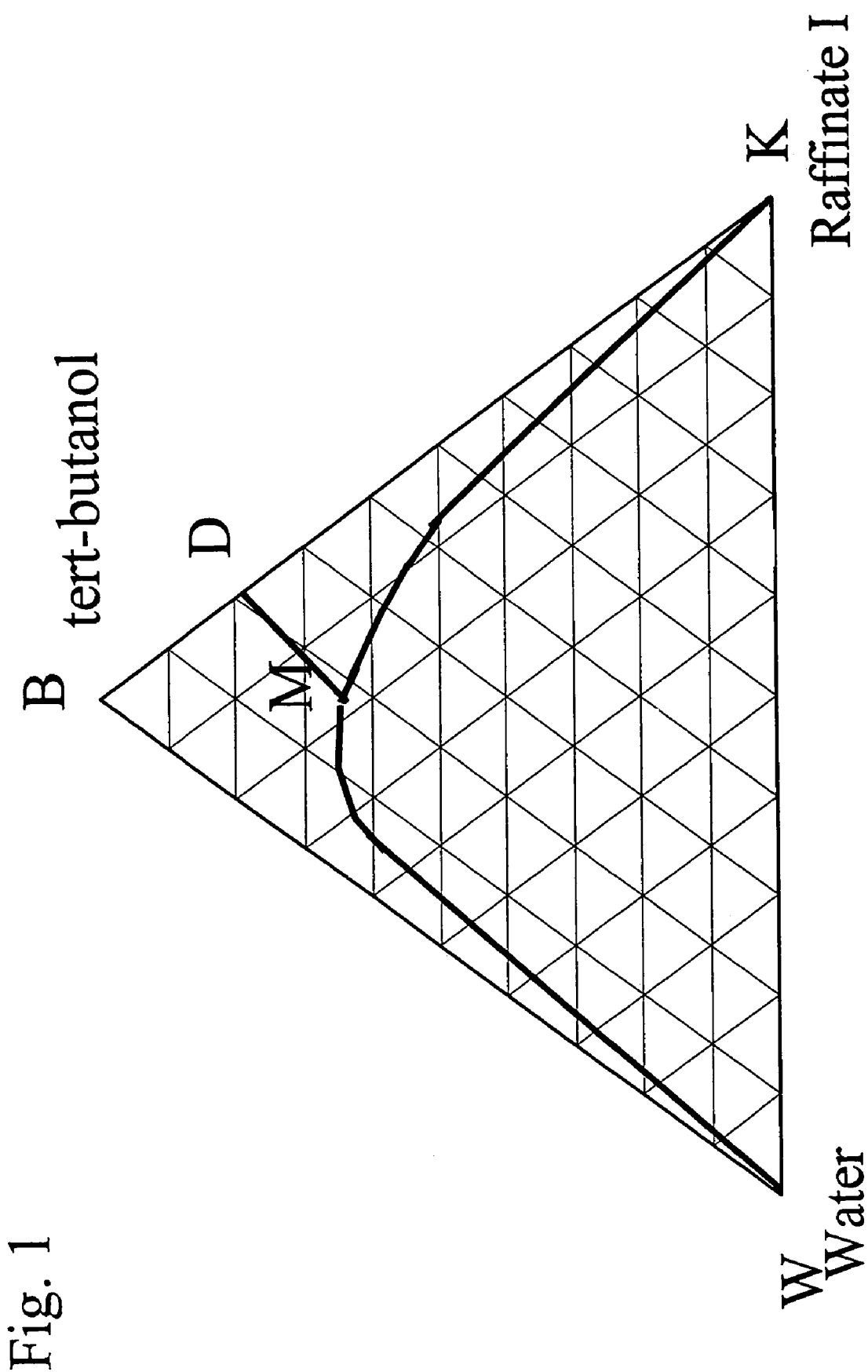
FIG. 1 shows a phase diagram for water, tert-butanol and an isobutene-containing hydrocarbon mixture.

The present invention accordingly provides a process for preparing tert-butanol by reaction of a homogeneous reaction mixture of water, tert-butanol and an isobutene-containing hydrocarbon mixture over an acidic ion-exchange resin at from 30 to 120° C., wherein the homogeneous reaction mixture at the start of the reaction has a proportion by mass of isobutene of over 10% by mass and a proportion of water which is from 30 to 80% of the amount of water which is possible on the basis of the solubility of water in the reaction mixture.

The proportion of water in the reaction mixture is preferably lower, e.g. 50–80%, 60–30% or 70–80%. These figures are in each case based on the maximum amount of the main amount defined by the solubility of water in the homogeneous reaction mixture.

According to the law of mass action for the reaction of isobutene with water to give TBA, equation 1 applies:

$$C_B = K \cdot C_I \cdot C_W \quad \text{(eq. 1)}$$

$C_B$: molar concentration of tert-butanol in the reaction mixture $C_I$: molar concentration of isobutene in the reaction mixture $C_W$: molar concentration of water in the reaction mixture K: equilibrium constant The following equation applies to the rate of tert-butanol formation in the reaction of a homogeneous tert-butanol/water/isobutene solution (E. Velo, L. Puigjaner, F. Recasens, Inhibition by Product in the Liquid-Phase-Hydration of Isobutene to tert-Butyl Alcohol:Kinetic and Equilibrium Studies, Ind. Eng. Chem. Res. 1988, 27, 2224–2231):

$$r = k(C_I \cdot C_W - C_B/K):(1 + c \cdot C_B)^n \ n = 1 \text{ or } 2 \quad \text{(eq. 2)}$$

r: reaction rate k and c are constants at a given temperature, catalyst and amount of catalyst.

According to this equation, the reaction rate for the formation of tert-butanol increases with increasing concentration of water. Accordingly, the maximum possible amount of water is used in WO 99/33775 and DE 030 25 262 when using a homogeneous solution.

It is therefore all the more surprising that the maximum reaction rate for the formation of tert-butanol at a given isobutene/tert-butanol ratio is found to be achieved not when using a solution saturated with water but when using mixtures having a lower water content.

In the reaction of a homogeneous mixture of an isobutene-containing hydrocarbon mixture (e.g. raffinate I), tert-butanol and water over an acidic ion-exchange resin, the reaction rate for the formation of tert-butanol is time dependent when the parameters are constant. Depending on the water content of the ion-exchange resin used, the initial rate of TBA formation can drop or increase. Starting with a resin having a low water content, the rate of tert-butanol formation initially decreases and becomes constant only after 2–6 days. During the same time, the catalyst absorbs water, as can easily be determined from the water balance. The amount of water absorbed by the catalyst is dependent on the water concentration of the reaction mixture and on the distance the water concentration is away from the solubility limit. The closer the water concentration to the solubility limit, the greater the amount of water taken up by the catalyst. As the water absorbed by the catalyst increases, the reaction rate for the formation of tert-butanol decreases under otherwise identical conditions. The reason for this could be the reduction in the acid strength of the active centers caused by hydration and/or inhibition of mass transfer, in particular for isobutene, by the water-containing swollen layer of the catalyst. The water content of the starting mixture thus influences the reaction rate for the formation of tert-butanol in long-term operation in two ways, namely by means of the concentration effect (cf. equation 2) which increases the rate and by the water absorption of the catalyst which reduces the rate.

The economics of an industrial process are determined not by the initial rates but by the rate in the steady state, i.e. in long-term operation of a plant.

The composition of a homogeneous mixture for the process of the invention is illustrated with the aid of a phase diagram. FIG. 1 shows the phase diagram for water, tert-butanol and an isobutene-containing hydrocarbon mixture in a triangular coordinate system (coordinates from 0 to 100% by mass). The hydrocarbon mixture (raffinate I) comprises 45% of isobutene and 55% of saturated and monounsaturated $C_4$-hydrocarbons. The phase diagram applies for a temperature range from 20 to 80° C. and a pressure above the saturation pressure of the hydrocarbon mixture. In this region, there is virtually no pressure and temperature dependence. This diagram changes little at other compositions of the isobutene-containing hydrocarbon mixture, so that it is suitable for explaining the invention. The curve from one apex W of the triangle via the maximum M to the other apex K of the triangle represents the boundary between the homogeneous region and the heterogeneous region. Below the curve, the mixture is heterogeneous, while the area above the curve is the region of homogeneous solutions. The curve also indicates the maximum proportion of water in the three-component system for a homogeneous solution to be obtained.

In the process of the invention, the reactor feed preferably has a composition which in FIG. 1 is in the area bounded by the section KM of the curve, the line MD and the line DK. The precise composition of the mixture at the beginning of the reaction is further within this area because of the low water content specified according to the invention. MD is the perpendicular from M to the baseline KB. It represents the composition of the mixture when the water concentration is reduced from point M at a constant hydrocarbon/tert-butanol ratio.

In the temperature range from 40 to 90° C., the maximum water content (solubility curve) for the three-component mixture (tert-butanol/water/raffinate I containing 45% of isobutene) can be calculated by means of the empirical equations below for the region of interest (line KM). These equations are also valid when the isobutene-containing hydrocarbon mixture has a different composition.

$$\ln X_W = 0.0570 X_B - 0.8215 \tag{eq. 3a}$$

or $$X_W = \text{EXP}[0.0570 X_B - 0.8215] \tag{eq. 3b}$$

where $X_W$: water content in % by mass $X_B$: tert-butanol content in % by mass In the process of the invention, the water content of the homogeneous reactor feed solution is accordingly lower than the maximum value which would be possible (line KM). It is from 30 to 80%, in particular from 50 to 0.80%, 60–80% or 70–80% of the amount of water made possible by the solubility of water in the mixture of tert-butanol and the isobutene-containing hydrocarbon mixture and can be determined by means of simple experiments or calculated using equation 3 a/b.

According to the invention, the isobutene concentration in the reactor feed is above 10% by mass, in particular above 15% by mass. The reactor feeds are thus mixtures whose compositions in the preferred temperature range from 35° C. to 70° C. are far removed from the thermodynamic equilibrium between isobutene, water and TBA.

As starting material, it is possible to use an isobutene-containing hydrocarbon mixture or else pure isobutene. The isobutene-containing hydrocarbon mixture preferably contains no acetylene derivatives, less than 5 000 ppm of dienes and no further olefins having one or more branches on the olefinic double bond.

Industrial mixtures containing isobutene are, for example, light petroleum spirit fractions from refineries, $C_4$ fractions from FCC plants or steamcrackers, mixtures from Fischer-Tropsch syntheses, mixtures from the dehydrogenation of butanes, mixtures from skeletal isomerization of linear butenes, mixtures formed by metathesis of olefins or other industrial processes.

These mixtures are used in the process of the invention, if desired after removal of the multiply unsaturated compounds. For example, a suitable isobutene mixture can be obtained from the $C_4$ fraction from a steamcracker by extraction of butadiene or by selective hydrogenation of the butadiene to linear butenes. This feed stock (raffinate I or selectively hydrogenated $C_4$ cracker fraction) comprises n-butane, isobutane, the three linear butenes and isobutene and is a preferred starting material for the process of the invention.

Raffinate I, hydrogenated $C_4$ cracker fraction or a hydrocarbon mixture having a similar composition could optionally be hydroisomerized in a reaction column. A mixture of isobutene, (possible 1-butene) and isobutane can be obtained in this way.

The concentration of isobutene in the hydrocarbon mixture can vary within a wide range. However, in the interests of the economics of the process, it is advisable to use hydrocarbon mixtures having an isobutene concentration of greater than 30% by mass, preferably greater than 40% by mass.

As catalyst, use is made of an acidic ion exchanger which is soluble neither in the starting material mixture nor in the product mixture. The catalyst must not introduce acidic substances into the product mixture by hydrolysis or other reactions under the reaction conditions, because this would lead to losses in yield in the work-up of the reaction mixture.

Suitable catalysts need to catalyze the hydration of isobutene but barely of the unbranched olefins under the reaction conditions. Furthermore, they must catalyze the oligomerization of olefins to no significant extent.

A suitable group of catalysts consists of solid ion-exchange resins having sulfonic acid groups. Particularly useful ion-exchange resins are, for example, resins prepared by sulfonation of phenol/aldehyde condensates or of cooligomers of aromatic vinyl compounds. Examples of aromatic vinyl compounds for preparing the oligomers are: styrene, vinyltoluene, vinylnaphthalene, vinylethylbenzene, methylstyrene, vinylchlorobenzene, vinylxylene and divinylbenzene. In particular, the cooligomers formed by reaction of styrene with divinylbenzene are used as precursor for the preparation of ion-exchange resins having sulfonic acid groups. The resins can be prepared so as to be in the form of gels, macroporous or sponge-like. Suitable resins of the styrene-divinylbenzene type are sold, inter alia, under the following trade names: Duolite C20, Duolite C26, Amberlyst 15, Amberlyst 35, Amberlite IR-120, Amberlite 200, Dowex 50, Lewatit SPC 118, Lewatit SPC 108, Lewatit K2611 (from Bayer), Lewatit K2631, OC 1501 (from Bayer), Lewatit K2621, Lewatit K2629, Lewatit K2431.

The properties of these resins, in particular specific surface area, porosity, stability, swelling or shrinkage and ion-exchange capacity, can be varied by means of the process used for their preparation.

In the process of the invention, the ion-exchange resins are preferably used in their H form. The ion exchange capacity is preferably from 2 to 7 eq/kg, in particular from 3 to 6 eq/kg (based on moist commercial resin).

Preference is given to using macroporous resins, for example Lewatit SPC 118, Lewatit SPC 108 or Lewatit K2631.

The particle size of the industrial resin is generally in the range from 0.5 to 2 mm. The particle size distribution can be selected so as to be narrower or wider. For example, ion-exchange resins having a very uniform particle size (monodisperse resin) can be used.

When a plurality of reactors are used, these can be charged with resin of the same or different particle size (or particle size distribution).

The ion-exchange resins can optionally be used as shaped bodies, for example cylinders, rings or spheres.

In the case of reactors through which flow at high linear velocities occurs, it can be advantageous to use a larger particle size in order to reduce the pressure drop, and in the case of reactors through which flow at a low linear velocity occurs, it can be advantageous to use a smaller particle size so as to achieve optimum conversion.

To avoid the elimination of acidic groups from the resin during operation, which could cause malfunctions in the work-up part of the process, and to maintain a high catalyst activity over a prolonged period of time, the ion-exchange resin can be pretreated, for example by washing with water, TBA or TBA/water mixtures in the temperature range from 40 to 120° C.

Since water is consumed by the hydration of isobutene, the water content of the reaction mixture drops. To obtain the highest possible yield and reaction rate, further water has to be fed in.

When using only one reactor, this can be achieved by, for example, feeding water in at various points along a tube reactor. However, it is difficult in practice to introduce precisely the necessary amount of water and to achieve immediate formation of a homogeneous solution. It is technically simpler and therefore advantageous to connect a plurality of reactors in series and to introduce the necessary amount of water between the reactors.

Since the concentration of tert-butanol rises as a result of the reaction, the solubility of water in the output from the reactor increases. It is therefore possible to add more water than has been reacted in the preceding reactor between the reactors. According to the invention, the water which has been consumed is replaced and, in addition, less water than would be necessary to reach the solubility limit is added. This can optionally be deviated from in the case of the last reactor and the latter can be supplied with a solution saturated with water or be supplied with a mixture containing somewhat more water than corresponds to the solubility. This has the advantage that the isobutene conversion is increased slightly at low isobutene concentrations when the reactor volumes are sufficiently large, but has the disadvantage that the tert-butanol/water ratio becomes less favorable for the work-up by distillation, particularly when a high proportion of anhydrous tert-butanol is to be obtained.

The amount of water in the starting material mixture originates from a tert-butanol/water solution which, with the exception of the start-up phase, is obtained in the process itself after hydrocarbons have been separated off, i.e. by recycling of part of the output from the reactor. If this amount of water is not sufficient, additional water is fed in. Between the reactors, pure water or a mixture of water with tert-butanol can be introduced. It is also possible for part of the TBA obtained by means of the reaction to be recycled for the preparation of a homogeneous mixture with water and the isobutene-containing hydrocarbon mixture. Water can be fed in between the reactors to alter the equilibrium of the reaction.

According to the invention, only homogeneous solutions are fed to the reactors. Water or water/tert-butanol solutions therefore have to be mixed with the starting hydrocarbon mixture or a reactor output so that a homogeneous solution has been formed before entry into the first reactor or one of the subsequent reactors. This can be achieved, for example, using a static mixer. The desired water concentration in the reactor feed is set by regulating the amounts of the individual streams after measurement of their water contents.

The process of the invention can be carried out in batch reactors or continuously operated reactors as are customarily used for solid/liquid contact reactions. When using continuously operated flow reactors, a fixed bed is usually, but not necessarily, employed. If a fixed-bed flow reactor is used, the liquid can flow upward or downward. Downward flow of the liquid is usually preferred.

Furthermore, the reactor can be operated with product recirculation or in a single pass.

When tube reactors are used, the ratio of length to diameter of the catalyst bed can be varied, either by means of the geometric dimensions of the reactor or via its degree of fill. It is thus possible to achieve different empty tube velocities at a constant amount of catalyst and space velocity (LHSV). Reactors in the case of which part of the reaction mixture is recirculated can be operated at empty tube velocities of typically from 13 to 26 m/h. In reactors which are operated in a single pass, the empty tube velocities are typically in the range from 1 to 13 m/h.

Accordingly, the space velocity of the catalyst (LHSV) in reactors which are operated with product recirculation is from 0.3 to 10 $h^{-1}$, in particular from 1 to 5 $h^{-1}$. In the case of reactors which are operated in a single pass, the space velocities are in the range from 0.1 to 5.0 $h^{-1}$, in particular in the range from 0.4 to 3 $h^{-1}$.

The process of the invention can be carried out in one reactor or in a plurality of reactors, in particular 2, 3 or 4 reactors, connected in series, which can have decreasing temperatures in the flow direction.

If the first reactor or a plurality of reactors is/are operated with product recirculation, a recirculation factor (ratio of quantity pumped around the circuit to fresh feed) of from 0.1 to 10 is set. The recirculation factor for the first reactor is preferably from 1 to 4, in particular from 2 to 3.5.

In a preferred process variant, the first reactor is carried out with product recirculation and the further reactors are carried out in a single pass. The number of reactors used is, depending on the desired conversion, typically from 2 to 10, in particular from 2 to 4.

Each reactor can be operated adiabatically or virtually isothermally, i.e. with a temperature rise of less than 10° C. An excessively high temperature rise should be avoided because of the adverse effect on the equilibrium (redissociation).

The temperatures at which the process of the invention is carried out are in the range from 30 to 120° C. At lower temperatures, the reaction rate is too low, and at higher temperatures there is increased occurrence of secondary reactions, for example oligomerization of olefins. The reactors are preferably operated in the temperature range from 35 to 70° C. The temperatures in the various reactors can be identical or different within the range indicated. In one process variant, the temperature is decreased from reactor to reactor in the flow direction. Since the position of the equilibrium becomes more favorable as the temperature drops, a higher conversion can be achieved in this way. However, it is not advisable to reduce the temperature to below 35° C., since the reaction then becomes too slow for an industrial process.

For example, in the case of four reactors connected in series, it is possible to react the first at a mean temperature of from 67 to 70° C., the second at a mean temperature of from 53 to 56° C., the third at a mean temperature of from 42 to 46° C. and the fourth reactor at from 42 to 38° C.

The reaction of the invention can be carried out at a pressure equal to or above the vapor pressure of the starting hydrocarbon mixture at the respective reaction temperature, preferably at a pressure below 40 bar. To avoid vaporization problems in the reactors, the pressure should be from 2 to 4 bar higher than the vapor pressure of the reaction mixture.

The total conversion of isobutene depends on the type and amount of catalyst used, the reaction conditions set and the number of reaction stages. For economic reasons, the isobutene conversion is kept in the range from 50 to 95%, preferably from 70 to 90%. It is also advisable, in order to maintain a high space-time yield, to use hydrocarbons having an isobutene content of not less than 20%, preferably not less than 40%.

The reaction mixture leaving the last reactor is passed to a distillation column which operates at or below the pressure of the last reactor, but at a pressure of at least 1 bar. The product obtained at the top of the distillation is a hydrocarbon mixture comprising unreacted butene and the "inert" hydrocarbons introduced with the starting material. The product obtained from the bottom is an aqueous tert-butanol solution.

The hydrocarbon mixture which has been separated off can be worked up to give further products of value. For example, if raffinate I or selectively hydrogenated $C_4$ fraction has been used as starting material, the product from the top comprises unreacted isobutene together with linear butenes and isobutane and n-butane. The residual isobutene can be separated off from this mixture by reaction with methanol to form methyl tert-butyl ether. In the remaining raffinate, the linear butenes can, optionally after 1-butene has been separated off, be converted into di-n-butene and their higher oligomers. Another use of the isobutene-free mixture is work-up to produce pure 1-butene.

Part of the aqueous tert-butanol solution obtained can be recirculated (recycled) to the process. The other part can be used as such or worked up to produce pure tert-butanol and an azeotrope of water and tert-butanol. It is also possible to recirculate another stream comprising water and tert-butanol which is obtained in the work-up of the crude tert-butanol to the first reactor.

The recirculation factor of the tert-butanol recycled in this way is preferably from 0.1 to 1.7.

Figure 3:
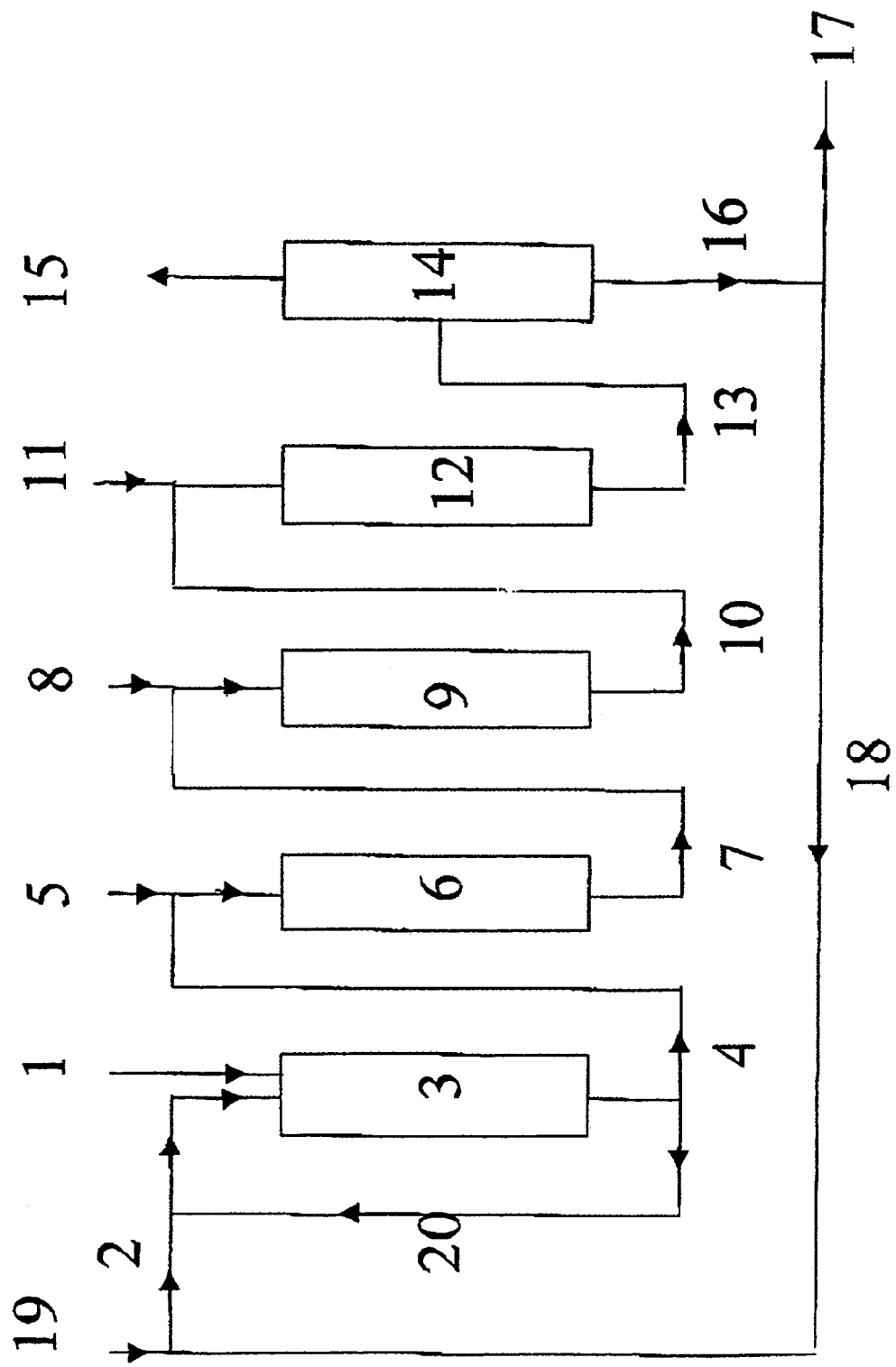
FIG. 3 shows a block diagram of a plant having four reactors for carrying out an embodiment of the invention process.

A block diagram of a plant having four reactors in which the process of the invention can be carried out continuously is shown in FIG. 3. An isobutene-containing hydrocarbon mixture 1 (for example raffinate I), output 20 from the first reactor 3 and a tert-butanol/water mixture 2 comprising a recycle stream 18 and, if appropriate, water 19 are fed into the first reactor 3. Part of the reactor output 4 is recirculated to the first reactor 3 and the other part is passed together with water 5 to the second reactor 6. The reactor output 7 is passed together with water 8 to the reactor 9. The reaction solution 10 together with water 11 is reacted in the reactor 12. The reactor output is fractionated in the column 14. The product 15 obtained at the top is a hydrocarbon mixture which comprises the hydrocarbons which are inert under the reaction conditions and small amounts of unreacted isobutene. The bottom product 16 consists essentially of tert-butanol and water. A part (18) of this is recirculated to the first reactor 3 while the other part (17) is used as such or is worked up in a distillation (not shown) to produce tert-butanol/water azeotrope and/or tert-butanol.

Thus, the tert-Butanol obtained according to the invention can be used as solvent and as intermediate for the preparation of methyl methacrylate. The tert-butanol can also be used to prepare peroxides such as peroxy ketals, peresters or dialkyl peroxides having at least one tertiary butyl group. These compounds are used as oxidants and as initiators for free-radical reactions, for example olefin polymerization or crosslinking of plastics. The tert-Butanol can also be used as intermediate in the isolation of pure isobutene from isobutene mixtures. Furthermore, the tert-butanol prepared according to the invention can be used for the introduction of tertiary butyl groups.

The following examples illustrate the invention but do not restrict its scope, which is defined by the description and the claims.

EXAMPLES

The raffinate stream used for experiments 1 to 6 had the following composition:

| n-Butane: | 8.2% |
|---|---|
| Isobutane: | 2.3% |
| 1-Butene: | 30.3% |
| 2-Butene (cis + trans): | 14.2% |
| Isobutene: | 45.0% |

The isobutene content of the raffinate is typically in the range from 30 to 60%.

Figure 2:
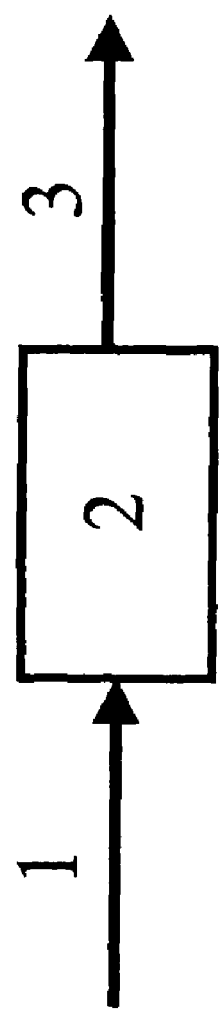
FIG. 2 shows a laboratory plant employed for carrying out an embodiment of the invention.

This raffinate stream was reacted with water and recirculated TBA as solubilizer in the existing production plant. The feed to the reactors of the production plant was used as feed for the laboratory experiments. FIG. 2 schematically shows the laboratory plant employed. The feed (1) was preheated to the desired temperature and fed into the laboratory reactor (2) which was operated isothermally at 60° C., except in experiments 3 and 4 where it was operated at 55° C. The reactor contained a fixed catalyst bed having a diameter of 1 cm and a length of 20 cm, except in experiments 3 and 4 where it had a length of 25 cm. The catalyst used was Amberlyst 35 in the $H^+$ form. The amount of catalyst was deliberately kept small in order to examine the effect of the water content more closely. The product stream (3) was analyzed by gas chromatography. The components n-butane, isobutane, 1-butene, 2-butene (cis+trans) are listed together as other $C_4$. The compositions reported are based on product outputs at pseudosteady-state equilibrium, which was reached after a time of from 20 to 30 hours. The pressure in the plant was 12 bar absolute.

Example 1

According to the Invention

The stream numbers in the following table were the same as in FIG. 2. Percentages are percent by mass. The feed (1) corresponded in terms of the isobutene content to the feed to the first reactor of the production plant. The feed rate was 0.3 kg/h.

| Stream number | Stream designation | Percent by mass |
|---|---|---|
| 1 | Reactor inlet | 21.87% of isobutene |
|   |   | 1.00% of water |
|   |   | 33.40% of TBA |
|   |   | 43.49% of other $C_4$ |
|   |   | 0.23% of other components |
| 3 | Reactor outlet | 20.72% of isobutene |
|   |   | 0.63% of water |
|   |   | 34.92% of TBA |
|   |   | 43.49% of other $C_4$ |
|   |   | 0.24% of other components |

The conversion achieved was: 5.30%

The proportion of water in the feed to the reactor relative to the proportion by mass of water at the miscibility gap was 35.39%.

Example 2

Comparison

The stream numbers in the following table were the same as in FIG. 2. Percentages are percent by mass. The feed (1) corresponded to the feed to the first reactor of the production plant. The feed rate was 0.3 kg/h.

| Stream number | Stream designation | Percent by mass |
|---|---|---|
| 1 | Reactor inlet | 21.58% of isobutene<br>2.31% of water<br>32.96% of TBA<br>42.92% of other $C_4$<br>0.23% of other components |
| 3 | Reactor outlet | 20.61% of isobutene<br>2.00% of water<br>34.25% of TBA<br>42.92% of other $C_4$<br>0.23% of other components |

The conversion achieved was: 4.53%

The proportion of water in the feed to the reactor relative to the proportion by mass of water at the miscibility gap was 83.66%.

Example 3

According to the Invention

The stream numbers in the following table were the same as in FIG. 2. Percentages are percent by mass. The feed (1) corresponded in terms of its isobutene content to the feed to the first reactor of the production plant. The feed rate was 0.3 kg/h. Unlike the other examples, the reaction temperature was (as in the case of the production plant) 55° C. A further difference compared to the other examples was that the catalyst bed had a length of 25 cm at a diameter of 1 cm.

| Stream number | Stream designation | Percent by mass |
|---|---|---|
| 1 | Reactor inlet | 15.42% of isobutene<br>2.00% of water<br>40.21% of TBA<br>42.06% of other $C_4$<br>0.13% of other components |
| 3 | Reactor outlet | 14.54% of isobutene<br>1.72% of water<br>41.38% of TBA<br>42.05% of other $C_4$<br>0.31% of other components |

The conversion achieved was: 5.73%

The proportion of water in the feed to the reactor relative to the proportion by mass of water at the miscibility gap was 49.38%.

Example 4

Comparison

The stream numbers in the following table were the same as in FIG. 2. Percentages are percent by mass. The feed (1) corresponded to the feed to the first reactor of the production plant. The feed rate was 0.3 kg/h. Unlike the other examples, the reaction temperature was (as in the case of the production plant) 55° C. A further difference compared to the other examples was that the catalyst bed had a length of 25 cm at a diameter of 1 cm.

| Stream number | Stream designation | Percent by mass |
|---|---|---|
| 1 | Reactor inlet | 15.21% of isobutene<br>3.31% of water<br>39.68% of TBA<br>41.49% of other $C_4$<br>0.30% of other components |
| 3 | Reactor outlet | 14.38% of isobutene<br>3.04% of water<br>40.77% of TBA<br>41.49% of other $C_4$<br>0.31% of other components |

The conversion achieved was: 5.47%

The proportion of water in the feed to the reactor relative to the proportion by mass of water at the miscibility gap was 84.07%.

Example 5

According to the Invention

The stream numbers in the following table were the same as in FIG. 2. Percentages are percent by mass. The feed (1) corresponded in terms of its isobutene content to the feed to the first reactor of the production plant, but at an isobutene content of 50% by mass in the raffinate I. The feed rate was 0.3 kg/h.

| Stream number | Stream designation | Percent by mass |
|---|---|---|
| 1 | Reactor inlet | 25.38% of isobutene<br>1.00% of water<br>33.38% of TBA<br>39.26% of other $C_4$<br>0.97% of other components |
| 3 | Reactor outlet | 23.90% of isobutene<br>0.53% of water<br>35.32% of TBA<br>39.26% of other $C_4$<br>0.98% of other components |

The conversion achieved was: 5.82%

The proportion of water in the feed to the reactor relative to the proportion by mass of water at the miscibility gap was 35.56%.

Example 6

Comparison

The stream numbers in the following table were the same as in FIG. 2. Percentages are percent by mass. The feed (1) corresponded to the feed to the first reactor of the production plant, but at an isobutene content of 50% by mass in the raffinate I. The feed rate was 0.3 kg/h.

| Stream number | Stream designation | Percent by mass |
|---|---|---|
| 1 | Reactor inlet | 25.00% of isobutene<br>2.50% of water |

| Stream number | Stream designation | Percent by mass |
|---|---|---|
| 3 | Reactor outlet | 32.88% of TBA<br>38.67% of other $C_4$<br>0.96% of other components<br>23.83% of isobutene<br>2.13% of water<br>34.42% of TBA<br>38.67% of other $C_4$<br>0.96% of other components |

The conversion achieved was: 4.67%
The proportion of water in the feed to the reactor relative to the proportion by mass of water at the miscibility gap was 91.09%.

Example 7

According to the Invention

The stream numbers in the following table were the same as in FIG. 2. Percentages are percent by mass. The feed (1) corresponded in terms of its isobutene content to the feed to the first reactor of the production plant, but at an isobutene content of 60% by mass in the raffinate I. The feed rate was 0.3 kg/h.

| Stream number | Stream designation | Percent by mass |
|---|---|---|
| 1 | Reactor inlet | 32.67% of isobutene<br>1.21% of water<br>33.32% of TBA<br>31.50% of other $C_4$<br>1.30% of other components |
| 3 | Reactor outlet | 30.52% of isobutene<br>0.52% of water<br>36.14% of TBA<br>31.50% of other $C_4$<br>1.32% of other components |

The conversion achieved was: 6.58%
The proportion of water in the feed to the reactor relative to the proportion by mass of water at the miscibility gap was 42.88%.

Example 8

According to the Invention

The stream numbers in the following table were the same as in FIG. 2. Percentages are percent by mass. The feed (1) corresponded to the feed to the first reactor of the production plant, but at an isobutene content of 60% by mass in the raffinate I. The feed rate was 0.3 kg/h.

| Stream number | Stream designation | Percent by mass |
|---|---|---|
| 1 | Reactor inlet | 32.34% of isobutene<br>2.20% of water<br>32.99% of TBA<br>31.18% of other $C_4$<br>1.29% of other components |
| 3 | Reactor outlet | 30.63% of isobutene<br>1.66% of water<br>35.24% of TBA<br>31.18% of other $C_4$<br>1.29% of other components |

The conversion achieved was: 5.28%
The proportion of water in the feed to the reactor relative to the proportion by mass of water at the miscibility gap was 79.72%.

Example 9

Comparison

The stream numbers in the following table were the same as in FIG. 2. Percentages are percent by mass. The feed (1) corresponded to the feed to the first reactor of the production plant, but at an isobutene content of 60% by mass in the raffinate I. The feed rate was 0.3 kg/h.

| Stream number | Stream designation | Percent by mass |
|---|---|---|
| 1 | Reactor inlet | 32.17% of isobutene<br>2.71% of water<br>32.82% of TBA<br>31.02% of other $C_4$<br>1.28% of other components |
| 3 | Reactor outlet | 30.61% of isobutene<br>2.21% of water<br>34.88% of TBA<br>31.02% of other $C_4$<br>1.29% of other components |

The conversion achieved was: 4.87%
The proportion of water in the feed to the reactor relative to the proportion by mass of water at the miscibility gap was 98.83%.

Example 10

Comparison

The stream numbers in the following table were the same as in FIG. 2. Percentages are percent by mass. The feed (1) corresponded to the feed to the first reactor of the production plant, but at an isobutene content of 60% by mass in the raffinate I. The feed rate was 0.3 kg/h.

| Stream number | Stream designation | Percent by mass |
|---|---|---|
| 1 | Reactor inlet | 32.84% of isobutene<br>0.70% of water<br>33.49% of TBA<br>31.66% of other $C_4$<br>1.31% of other components |
| 3 | Reactor outlet | 31.17% of isobutene<br>0.20% of water<br>35.57% of TBA<br>31.66% of other $C_4$<br>1.40% of other components |

The conversion achieved was: 5.06%
The proportion of water in the feed to the reactor relative to the proportion by mass of water at the miscibility gap was 24.79%.

Comparison of experiment 1 with experiment 2, of experiment 3 with experiment 4, of experiment 5 with experiment 6 and comparison of experiments 7, 8 and 9 indicates that in each case the experiments using the lowest water content give the highest conversions of isobutene into TBA.

Comparison of examples 7, 8 and 10 shows that when the water content goes below the claimed limit of at least 30% of water based on the proportion by mass of water at the miscibility gap, the achievable conversion drops again.

The invention claimed is:

1. A process for preparing tert-butanol comprising contacting a homogeneous reaction mixture comprising water, tert-butanol and an isobutene-containing hydrocarbon mixture with an acidic ion-exchange resin at from 30 to 120° C., wherein the homogeneous reaction mixture prior to said contacting has a proportion of isobutene of over 10% by mass and a proportion of water which is from 30 to 80% of the amount of water which is possible based on the solubility of water in the homogenous reaction mixture.

2. The process of claim 1, wherein the proportion of water is from 50 to 80% of the amount of water which is possible based on the solubility of water in the homogenous reaction mixture.

3. The process of claim 1, wherein the proportion of water is from 60 to 80% of the amount of water which is possible based on the solubility of water in the homogenous reaction mixture.

4. The process of claim 1, wherein the proportion of water is from 70 to 80% of the amount of water which is possible based on the solubility of water in the homogenous reaction mixture.

5. The process of claim 1, wherein the isobutene-containing hydrocarbon mixture is pure isobutene.

6. The process of claim 1, wherein the isobutene-containing hydrocarbon mixture does not comprise acetylene derivatives, comprises less than 5,000 ppm of dienes and no further olefins having one or more branches on the olefinic double bond.

7. The process of claim 1, wherein a part of the tert-butanol obtained by the process is recycled to prepare the homogeneous reaction mixture.

8. The process of claim 7, wherein the tert-butanol recycled at a recirculation factor from 0.1 to 1.7.

9. The process of claim 1, wherein the contacting is carried out in a plurality of reactors connected in series.

10. The process of claim 9, wherein water is introduced between the reactors.

11. The process of claim 9, wherein the contacting is carried out in at least four reactors.

12. The process of claim 9, wherein the plurality of reactors connected in series have decreasing temperatures in the flow direction.

13. The process of claim 12, wherein the contacting is carried out in at least four reactors.

14. The process of claim 13, wherein the temperature of the first reactor is from 67 to 70° C., the temperature of the second reactor is from 53 to 56° C., the temperature of the third reactor is from 42 to 46° C., and the temperature of the fourth reactor is from 42 to 38° C.

15. The process of claim 1, wherein the acidic ion-exchange resin comprises sulfonic acid groups.

16. The process of claim 1, wherein the proportion of isobutene in the isobutene-containing hydrocarbon mixture is at least 30% by mass.

17. The process of claim 1, wherein the proportion of isobutene in the isobutene-containing hydrocarbon mixture is at least 40% by mass.

18. The process of claim 1, further comprising:
after the contacting, using the tert-butanol in a process for preparing methylmethacrylate.

19. The process of claim 1, further comprising:
after the contacting, using the tert-butanol as a precursor for preparing a peroxide having at least one tertiary butyl group.

20. The process of claim 1, further comprising:
after the contacting, using the tert-butanol as an intermediate in the isolation of pure isobutene from an isobutene mixture.

* * * * *